(12) United States Patent
Dabney et al.

(10) Patent No.: US 7,853,325 B2
(45) Date of Patent: *Dec. 14, 2010

(54) CYLINDRICAL BANDSTOP FILTERS FOR MEDICAL LEAD SYSTEMS

(75) Inventors: Warren S. Dabney, Orchard Park, NY (US); Kenneth D. Billings, Aiken, SC (US); Bethany M. Hauser, Lockport, NY (US); Brenden Hill, Belfast, NY (US); Gabe Kustra, Cheektowaga, NY (US); Robert A. Stevenson, Canyon Country, CA (US)

(73) Assignee: Greatbatch Ltd., Clarence, NY (US)

( * ) Notice: Subject to any disclaimer, the term of this patent is extended or adjusted under 35 U.S.C. 154(b) by 531 days.

This patent is subject to a terminal disclaimer.

(21) Appl. No.: 11/943,854

(22) Filed: Nov. 21, 2007

(65) Prior Publication Data

US 2008/0116997 A1 May 22, 2008

Related U.S. Application Data

(63) Continuation-in-part of application No. 11/558,349, filed on Nov. 9, 2006, which is a continuation-in-part of application No. 11/423,073, filed on Jun. 8, 2006, which is a continuation-in-part of application No. 10/123,534, filed on Apr. 15, 2002, now abandoned.

(60) Provisional application No. 60/283,725, filed on Apr. 13, 2001, provisional application No. 60/803,672, filed on Jun. 1, 2006, provisional application No. 60/597,125, filed on Nov. 11, 2005, provisional application No. 60/968,662, filed on Aug. 29, 2007.

(51) Int. Cl.
*A61N 1/00* (2006.01)

(52) U.S. Cl. ........................................................ 607/2

(58) Field of Classification Search ..................... 607/2, 607/40, 115; 324/318
See application file for complete search history.

(56) References Cited

U.S. PATENT DOCUMENTS 3,871,382 A     3/1975   Mann (Continued)

FOREIGN PATENT DOCUMENTS

EP          0243573 A2    11/1987

(Continued)

OTHER PUBLICATIONS

Ariel Roguin, et al., Modern Pacemaker and Implantable Cardioverter/Defibrillator Systems Can Be Magnetic Resonance Imaging Safe, Circulation—Journal of the American Heart Association, Aug. 4, 2004 (originally published online Jul. 26, 2004), pp. 475-482, American Heart Association, Dallas, Texas, USA.

(Continued)

*Primary Examiner*—George Manuel
(74) *Attorney, Agent, or Firm*—Kelly Lowry & Kelley, LLP

(57) ABSTRACT

A one-piece cylindrical bandstop filter for medical lead systems incorporates parallel capacitive and inductive elements in a compact cylindrical configuration. The compact cylindrical configuration of the bandstop filter does not add significantly to the size or weight of the medical lead system. Preferably, the bandstop filters are of biocompatible materials or hermetically sealed in biocompatible containers. The parallel capacitive and inductive elements are placed in series with the medical lead system, and are selected so as to resonate at one or more selected frequencies, typically MRI pulsed frequencies.

42 Claims, 8 Drawing Sheets

U.S. PATENT DOCUMENTS

| | | | |
|---|---|---|---|
| 3,968,802 | A | 7/1976 | Ballis |
| 4,633,181 | A | 12/1986 | Murphy-Boesch et al. |
| 4,654,880 | A | 3/1987 | Sontag |
| 4,689,621 | A | 8/1987 | Kleinberg |
| 4,799,499 | A | 1/1989 | Bisping |
| 4,858,623 | A | 8/1989 | Bradshaw et al. |
| 5,136,244 | A * | 8/1992 | Jones et al. .................. 324/318 |
| 5,209,233 | A | 5/1993 | Holland et al. |
| 5,217,010 | A | 6/1993 | Tsitlik et al. |
| 5,246,438 | A | 9/1993 | Langberg |
| 5,300,108 | A | 4/1994 | Rebell et al. |
| 5,333,095 | A | 7/1994 | Stevenson et al. |
| 5,363,845 | A | 11/1994 | Chowdhury et al. |
| 5,398,683 | A | 3/1995 | Edwards et al. |
| 5,514,173 | A | 5/1996 | Rebell et al. |
| 5,545,201 | A | 8/1996 | Helland et al. |
| 5,629,622 | A | 5/1997 | Scampini |
| 5,697,958 | A | 12/1997 | Paul et al. |
| 5,716,390 | A | 2/1998 | Li |
| 5,722,998 | A | 3/1998 | Prutchi et al. |
| 5,741,321 | A | 4/1998 | Brennen |
| 5,751,539 | A | 5/1998 | Stevenson et al. |
| 5,759,202 | A | 6/1998 | Schroeppel |
| 5,905,627 | A | 5/1999 | Brendel et al. |
| 5,959,829 | A | 9/1999 | Stevenson et al. |
| 5,964,705 | A | 10/1999 | Truwit et al. |
| 5,973,906 | A | 10/1999 | Stevenson et al. |
| 5,978,204 | A | 11/1999 | Stevenson |
| 6,008,980 | A | 12/1999 | Stevenson et al. |
| 6,055,457 | A | 4/2000 | Bonner |
| 6,101,417 | A | 8/2000 | Vogel et al. |
| 6,141,594 | A | 10/2000 | Flynn et al. |
| 6,159,560 | A | 12/2000 | Stevenson et al. |
| 6,236,205 | B1 | 5/2001 | Luedeke et al. |
| 6,275,369 | B1 | 8/2001 | Stevenson et al. |
| 6,280,385 | B1 | 8/2001 | Melzer et al. |
| 6,424,234 | B1 | 7/2002 | Stevenson |
| 6,456,481 | B1 | 9/2002 | Stevenson |
| 6,473,291 | B1 | 10/2002 | Stevenson |
| 6,493,591 | B1 | 12/2002 | Stokes |
| 6,529,103 | B1 | 3/2003 | Brendel et al. |
| 6,535,766 | B1 | 3/2003 | Thompson et al. |
| 6,539,253 | B2 * | 3/2003 | Thompson et al. ............. 607/2 |
| 6,566,978 | B2 | 5/2003 | Stevenson et al. |
| 6,567,259 | B2 | 5/2003 | Stevenson et al. |
| 6,567,703 | B1 | 5/2003 | Thompson et al. |
| 6,606,513 | B2 | 8/2003 | Lardo et al. |
| 6,643,903 | B2 | 11/2003 | Stevenson et al. |
| 6,675,033 | B1 | 1/2004 | Lardo et al. |
| 6,675,779 | B2 | 1/2004 | King et al. |
| 6,687,550 | B1 | 2/2004 | Doan |
| 6,701,176 | B1 | 3/2004 | Halperin et al. |
| 6,765,780 | B2 | 7/2004 | Brendel et al. |
| 6,832,114 | B1 * | 12/2004 | Whitehurst et al. ........... 607/40 |
| 6,847,837 | B1 | 1/2005 | Melzer et al. |
| 6,868,288 | B2 | 3/2005 | Thompson |
| 6,876,885 | B2 | 4/2005 | Swoyer et al. |
| 6,882,248 | B2 | 4/2005 | Stevenson et al. |
| 6,898,454 | B2 | 5/2005 | Atalar et al. |
| 6,925,328 | B2 | 8/2005 | Foster et al. |
| 6,931,286 | B2 | 8/2005 | Sigg et al. |
| 6,949,929 | B2 | 9/2005 | Gray et al. |
| 6,952,613 | B2 | 10/2005 | Swoyer et al. |
| 6,971,391 | B1 | 12/2005 | Wang et al. |
| 6,985,347 | B2 | 1/2006 | Stevenson et al. |
| 6,999,818 | B2 | 2/2006 | Stevenson et al. |
| 7,013,180 | B2 | 3/2006 | Dougherty et al. |
| 7,092,766 | B1 | 8/2006 | Salys et al. |
| 7,113,387 | B2 | 9/2006 | Stevenson et al. |
| 7,123,013 | B2 | 10/2006 | Gray |
| 7,155,271 | B2 | 12/2006 | Halperin et al. |
| 2003/0028094 | A1 | 2/2003 | Kumar et al. |
| 2003/0050557 | A1 | 3/2003 | Susil et al. |
| 2004/0167392 | A1 | 8/2004 | Halperin et al. |
| 2004/0263174 | A1 | 12/2004 | Gray et al. |
| 2005/0197677 | A1 | 9/2005 | Stevenson |
| 2006/0009819 | A1 | 1/2006 | Przybyszewski |
| 2006/0100506 | A1 | 5/2006 | Halperin et al. |

FOREIGN PATENT DOCUMENTS

| | | |
|---|---|---|
| EP | 0145430 B1 | 5/1991 |
| EP | 1021730 B1 | 4/1994 |
| EP | 0 498 996 B1 | 3/1997 |
| EP | 0930509 B1 | 12/1998 |
| JP | 60141034 | 7/1985 |
| JP | 61181926 | 8/1986 |
| JP | 62233905 | 10/1987 |
| JP | 4071536 | 3/1992 |
| JP | 6054823 | 3/1994 |
| JP | 11239572 | 9/1999 |
| WO | WO 99/19739 | 4/1999 |
| WO | WO 02/083016 A1 | 10/2002 |

OTHER PUBLICATIONS

Robert C. Susil, Christopher J. Yeung, Henry R. Halperin, Albert C. Lardo, Ergin Atalar, Multifunctional Interventional Devices for MRI: A Combined Electrophysiology/MRI Catheter, Magnetic Resonance in Medicine, 2002, pp. 594-600, Wiley-Liss, Inc., Departments of Biomedical Engineering, Radiology & Medicine, Johns Hopkins University School of Medicine, Baltimore, Maryland.

Robert C. Susil, Ergin Atalar, Albert Lardo, Multifunctional Interventional Devices for Use in MRI, U.S. Appl. No. 60/283,725, filed Apr. 13, 2001.

* cited by examiner

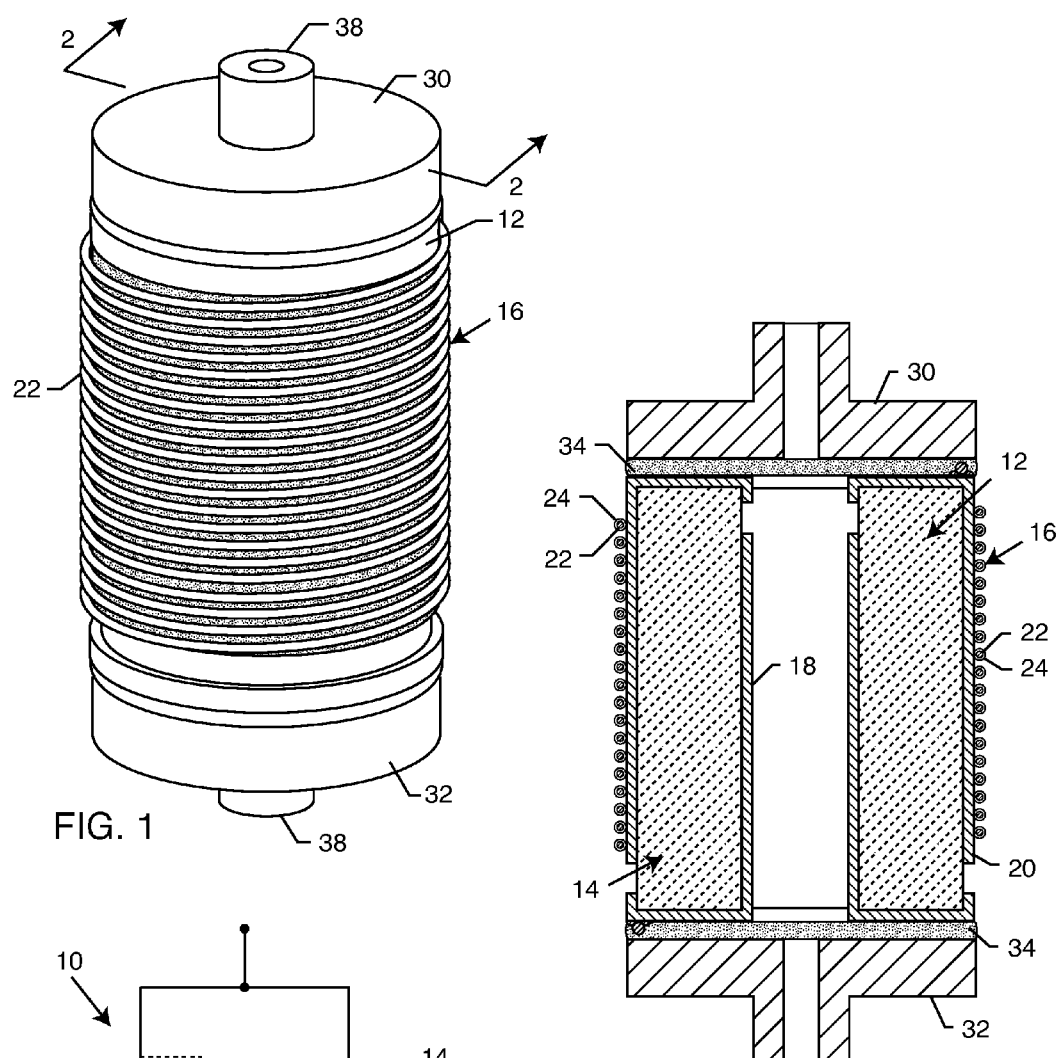
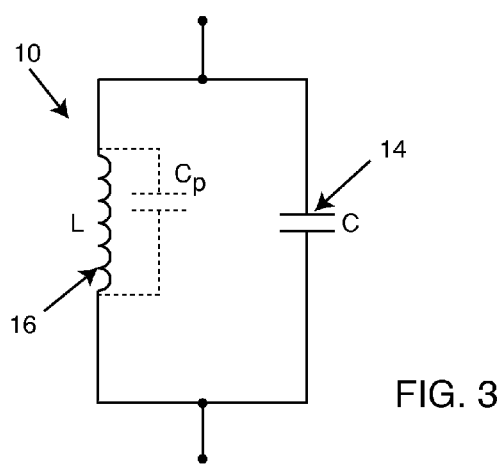
FIG. 1
FIG. 2
FIG. 3

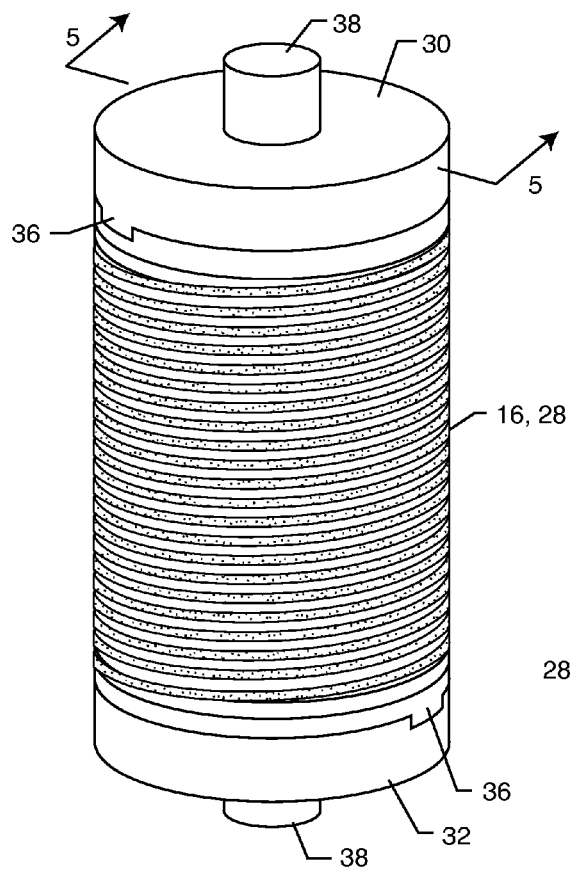
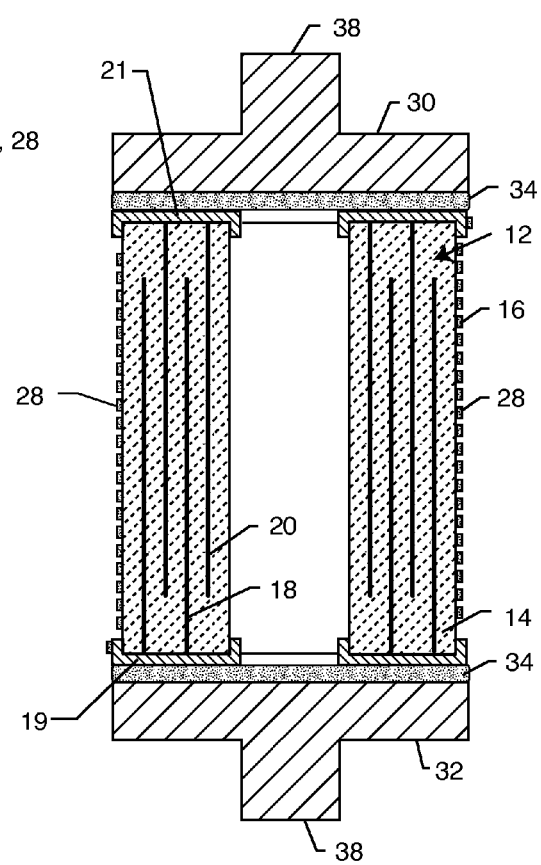
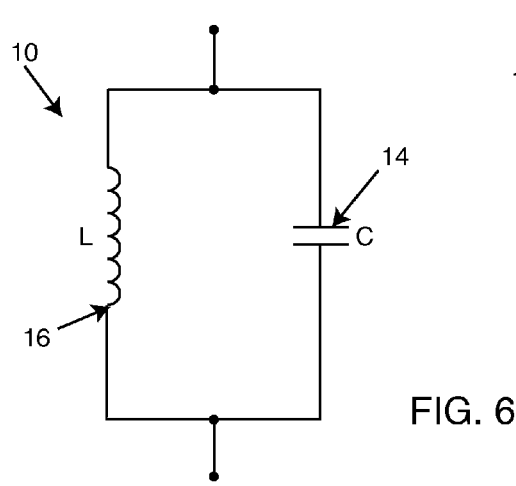
FIG. 4
FIG. 5
FIG. 6

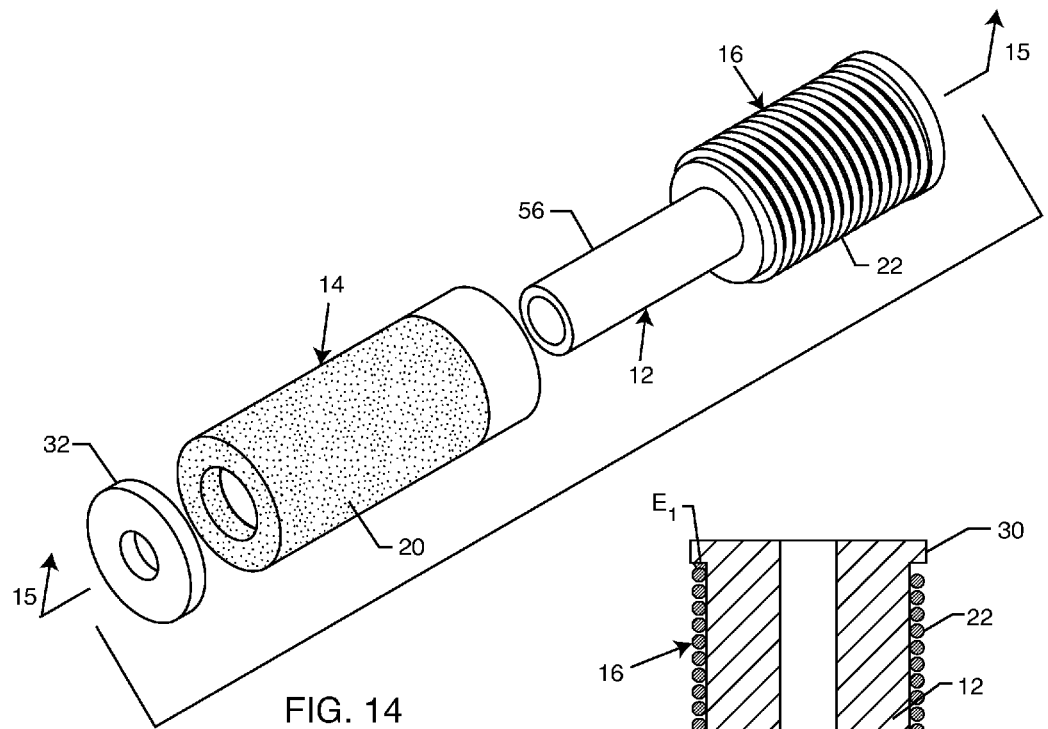
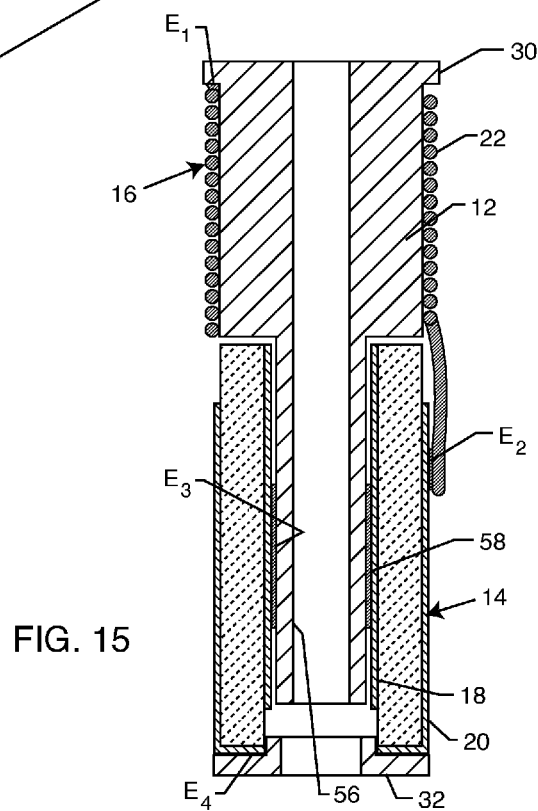
FIG. 14
FIG. 15

CYLINDRICAL BANDSTOP FILTERS FOR MEDICAL LEAD SYSTEMS

BACKGROUND OF THE INVENTION

Magnetic resonance imaging (MRI) is currently contraindicated for patients who have implanted medical devices. This is due largely to the patient safety issue that results when the strong electromagnetic fields of an MRI system interact with the antenna-like therapy delivery leads of an active implantable medical device. It is well documented that the RF signals that are generated by the MRI system can attenuate along the length of a lead body and create induced current loops. These current loops can cause significant heating at points of high current concentration, the most significant of which is the distal tip, where the lead system makes direct contact with myocardial tissue.

As disclosed in U.S. patent application Ser. No. 11/558,349 filed Nov. 9, 2006, the contents of which are incorporated herein by reference, a novel method to minimize the expected heating at the distal tip is to incorporate a bandstop filter. This bandstop filter is comprised of an inductor and capacitor in parallel, with the entire filter connected in series to the lead system. In such a system, the bandstop filter can be constructed so that its resonant frequency or frequencies coincides with the RF operating frequency of one or more MRI systems. RF frequencies are directly related to the standing magnetic field by the Lamour Relationship. Typical values are 64 MHz for 1.5 T systems, and 128 MHz for 3.0 T systems.

Implementation of this technology in implantable leads is a significant challenge. Bandstop filters for use in lead systems must be biocompatible, not significantly change the electrical characteristics of the lead (except within the context of the invention), and must not add significant size or weight. With increasingly smaller leads being developed to accommodate small vasculature and left ventricular pacing through the coronary sinus, bandstop technology must be equally scalable to match the same demands.

The present invention satisfies these needs and provides other related advantages.

SUMMARY OF THE INVENTION

The present invention is directed to bandstop filters for use in medical lead systems which do not add significant size or weight to the lead system. The bandstop filters of the present invention are comprised of an inductor and capacitor in parallel, and connected in series to the lead system, and configured to attenuate current flow through a lead wire at a selected frequency.

In one embodiment, the medical lead bandstop filter comprises a tubular capacitor having a first electrode and a second electrode. A generally cylindrical inductor is attached in series at an end of the capacitor. The inductor includes a winding having a first end conductively coupled to the first electrode and a second end conductively coupled to the second electrode so as to place the capacitor and the inductor electrically in parallel with one another. Values of capacitance and inductance are selected such that the bandstop filter is resonant at a selected frequency, or range of selected frequencies, typically corresponding to a plurality of MRI pulsed frequencies.

The inductor includes a protruding section extending into an adjacent end of the capacitor. The protruding section comprises a conductive material conductively coupled to the first electrode.

The inductor includes a head section comprised of insulative material coupled to the protruding section and associated with the winding. The winding comprises a conductive circuit trace or wire attached to an outer surface of the head section. A first end cap is conductively coupled to the first end of the winding and the first electrode. A second end cap is conductively coupled to the second end of the winding and the second electrode.

Preferably, the electrical components of the medical lead bandstop filter are hermetically insulated from contact with biological fluids or cells. This may be accomplished by coating the bandstop filter with a biocompatible material. Alternatively, the bandstop filter is comprised of biocompatible materials. In yet another embodiment, the bandstop filter is disposed within a biocompatible cylinder having a first biocompatible end cap attached to a first end thereof, and a second biocompatible end cap attached to a second end thereof so as to prevent body fluids or cells from entering therein. The first end of the inductor winding and the capacitor first electrode are conductively coupled to the first end cap. The second end of the inductor and the capacitor second electrode are conductively coupled to the second end cap. The first and second end caps are adapted to be conductively coupled to the lead wire or an electrode of a medical lead system. In one embodiment, a tube extends through the first end cap and into the cylinder so as to be conductively coupled to the first electrode. The tube may extend through the cylinder and the second end cap.

In another embodiment, the medical lead bandstop filter comprises a generally cylindrical dielectric body. A conductive winding is associated with the body so as to form an inductor. Turns of the conductive winding form a parasitic capacitor in parallel with the inductor. Values of capacitance and inductance are selected such that the bandstop filter is resonant and attenuates current flow through a lead wire at a selected frequency. The selected frequency may comprise a range of selected frequencies, typically corresponding to a plurality of MRI pulse frequencies.

The generally cylindrical dielectric body may be tubular. The conductive winding may be attached to an outer surface of the body and comprise a conductive wire or a conductive circuit trace. Alternatively, the conductive winding may be embedded within the dielectric body.

Preferably, the electrical components of the bandstop filter are hermetically insulated from contact with biological fluids or cells. The bandstop filter may be comprised of biocompatible materials. Alternatively, the bandstop filter may be hermetically sealed within a biocompatible material coating the bandstop filter. In yet another embodiment, the bandstop filter is disposed within a biocompatible cylinder having a first biocompatible end cap attached to a first end thereof, and a second biocompatible end cap attached to a second end thereof so as to prevent body fluids or cells from entering therein. The first end of the inductor winding is conductively coupled to the first end cap, and the second end of the inductor winding is conductively coupled to the second end cap. The first and second end caps are adapted to be conductively coupled to the lead wire or an electrode of the medical lead system.

In yet another embodiment, the medical lead bandstop filter comprises a tubular capacitor having a first electrode and a second electrode. The first electrode may comprise a first set of electrode plates, and the second electrode may comprise a second set of electrode plates in spaced apart and overlapping relation with the first set of electrode plates. A conductive winding is wound around the capacitor and forms an inductor. A first end of the winding is conductively coupled to the first electrode. A second end of the winding is conductively coupled to the second electrode, so as to place the capacitor and the inductor in parallel with one another. The conductive winding may comprise a wire attached to an outer surface of the tubular capacitor. Alternatively, the conductive winding may comprise a conductive circuit trace attached to an outer surface of the tubular capacitor.

Values of capacitance and inductance are selected such that the bandstop filter is resonant and attenuates current flow through a lead wire at a selected frequency. Typically, the selected frequency comprises a range of selected frequencies. The selected range of frequencies typically correspond to a plurality of MRI pulsed frequencies.

Preferably, electrical components of the medical lead bandstop filter are hermetically insulated from contact with biological fluids or cells. For example, the bandstop filter may be comprised of biocompatible materials. Alternatively, the bandstop filter may be hermetically sealed within a biocompatible material coating the bandstop filter. In yet another embodiment, the bandstop filter is disposed within a biocompatible cylinder having a first biocompatible end cap attached to a first end thereof, and a second biocompatible end cap attached to a second end thereof so as to prevent body fluids or cells from entering therein. The first and second end caps are adapted to be conductively coupled to a lead wire or an electrode of a medical lead system. The first end of the inductor winding and the capacitor first electrode are conductively coupled to the first end cap. The second end of the inductor and the capacitor second electrode are conductively coupled to the second end cap, so as to place the medical lead bandstop filter in series with the medical lead wire. A tube may extend through the first end cap and into the cylinder, and in some cases through the cylinder and the end cap, so as to be conductively coupled to the first electrode.

Other features and advantages of the present invention will become apparent from the following more detailed description, taken in conjunction with the accompanying drawings, which illustrate, by way of example, the principles of the invention.

BRIEF DESCRIPTION OF THE DRAWINGS

The accompanying drawings illustrate the invention. In such drawings:

FIG. 1 is a perspective view of a cylindrical bandstop filter for medical lead systems embodying the present invention;

FIG. 2 is a sectional view taken generally along the line 2-2 of FIG. 1;

FIG. 3 is an electrical schematic view of the tank filter formed by the structure shown in FIGS. 1 and 2;

FIG. 4 is a perspective view of an alternative cylindrical bandstop filter for medical lead systems embodying the present invention;

FIG. 5 is a sectional view taken generally along the line 5-5 of FIG. 4;

FIG. 6 is an electrical schematic view of the tank filter formed by the structure shown in FIGS. 4 and 5;

FIG. 14 is an exploded perspective view of another cylindrical bandstop filter for medical lead systems embodying the present invention, similar to that shown in FIG. 10;

FIG. 15 is an enlarged sectional view taken generally along the line 15-15 of FIG. 14, illustrating the cylindrical bandstop filter in its assembled configuration;

DETAILED DESCRIPTION OF THE PREFERRED EMBODIMENTS

Figure 7:
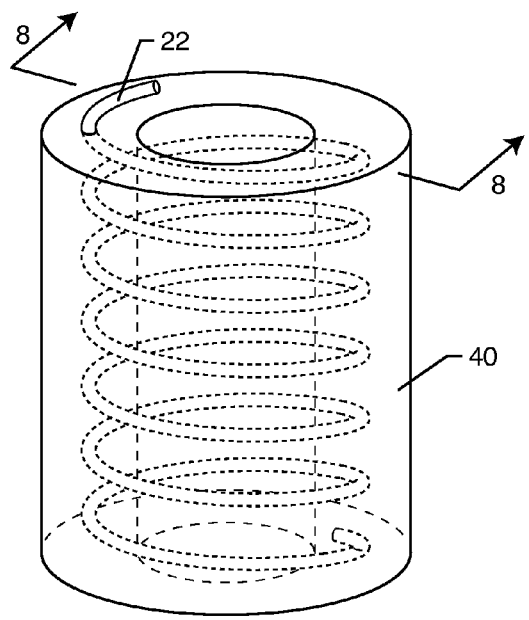
FIG. 7 is a perspective view of another alternative cylindrical bandstop filter for medical lead systems embodying the present invention.

The present invention describes a novel way to build a parallel inductor and capacitor circuit 10 in such a way that it is comprised of a single, cylindrical substrate 12, typically comprised of dielectric material. In this manner, the component can retain the cylindrical shape of the lead system, and be directly portable to existing lead technologies.

The cylindrical substrate 12 can be hollow, comprising an outer diameter and an inner diameter, as needed. The aspect ratio between outer diameter and inner diameter is dependent on lead design, specific strength requirements, and required electrical performance. The single substrate is effectively split into two portions, one comprising the capacitive element 14, and the other comprising the inductive element 16. The capacitive element 14 and inductive element 16 are in parallel with one another, electrically, and are selected so as to resonate at one or more frequencies, typically MRI pulsed frequencies.

With reference now to FIGS. 1-3, in one embodiment, the capacitive element 14 includes first and second electrode plates 18, 20, used to generate the capacitive response. A dielectric body substrate 12, which is generally cylindrical, and more typically tubular in configuration as illustrated, is an extruded or pressed piece of substrate, typically dielectric material. The positive 18 and negative 20 electrodes are placed along the inner diameter (ID) and the spaced apart surface outer diameter (OD), respectively (note: designation of positive and negative in this case is arbitrary, but useful for descriptive reasons). In this case, the capacitance is generated by the overlapping cross-sectional area between the two plates, and the dielectric thickness is defined as one-half the difference between the OD and the ID.

With reference now to FIGS. 4-6, in another embodiment, the capacitor 14 is created through the use of prior art multi-layer tubular capacitor technology, and is built up through successive stacking of appropriate ceramic green tapes (or other materials) which are then rolled prior to scintering into the tubular structure as shown. In this case, positive 18 and negative 20 electrodes are printed onto successive tape layers, and the capacitor's dielectric thickness is defined as the fired thickness of the tape layers. In this manner, capacitance can be linearly increased by increasing the number of plate sets during stacking. Metallization 19 is attached to one end, or surface of the body 12 and conductively coupled to the positive electrode plates 18. Metallization 21 is disposed on the generally opposite side or surface of the body 12, and is conductively coupled to the negative electrodes 20, to create a multi-layer tubular capacitor 14.

As shown in FIGS. 1-2 and 4-5, the inductor 16 is formed around the outer diameter 12 of the substrate using one of two methods. The first method shown in FIGS. 1 and 2 is to use high-gauge thin wire 22, which is wound about the cylinder body 12 an appropriate number of times to generate the necessary inductance, as described by the appropriate equations. The wire 22 can be comprised of any appropriate conductive material (Cu, Au, Ag, Pt/Ir, MP-35N and the like), and is coated with an insulative layer 24. Resistance through the circuit 10 can be changed by changing the gauge of the wire (e.g., 34 American Wire Gauge (AWG) vs. 39 AWG), or changing the conductive material itself (change in resistivity). The winding is then affixed to the substrate 12 using an appropriate adhesive, such as epoxy, polyimide, or other similar material.

Another method of creating the inductor 16 shown in FIGS. 4 and 5 is to use thick, thin film, plating methods or sputtering to create circuit traces 28. A preferred iteration is photolithography/photoetching, which are well-defined arts. The conductive traces 28 can be composed of any depositable conductive material or alloy, including copper, silver, gold, platinum, iridium, or the like. In this manner, resistance of the part can be effectively controlled by changing the thickness and width of the resulting traces. Since resistance is dependent on the cross-sectional area of the trace, increasing these dimensions can result in highly tailorable resistive characteristics, with minimal impact on the inductive performance. Additionally, changing the conductive material (thereby changing the resistivity), is another way to control these characteristics.

End connectors 30 and 32 are attached to either end of the substrate body 12. These connectors are comprised of a conductive material suitable for providing weld or solder connections for lead-related components, such as MP35N strands or passive/active lead tips. The connectors 30 and 32 are attached using conductive polyimide, conductive epoxy, or brazing materials 34. Additionally, the caps (and the substrate tubes) can be machined to include notch features 36, as shown in FIG. 4, to create higher torsional strength in the joint. Electrical connection between the electrical components on the tube is created through the use of end terminations, or the extension of the appropriate capacitive and inductive elements along the OD and ID of the substrate. The preferred design of these connectors is cylindrical, as is the substrate body 12. Counterbored tabs 38 extend from the junction point of these connectors, to provide an attachment point for the lead or tissue electrode components. These connectors can be hollow for guide wire insertion, as illustrated in FIGS. 1 and 2, and the dimension of the smaller tab can be varied.

The end connectors 30 and 32 can be made of a variety of biocompatible materials. It is important that these be conductive and also suitable for convenient laser weld attachment of the implantable device lead wire system. Common lead wires systems are made from wires of MP-35N alloy. Accordingly, the end connectors 30 and 32 could be made of gold, platinum, palladium, titanium, or MP-35N, or alloys of all of the above materials.

Referring once again to FIGS. 1 and 2, it will be appreciated that the wire 22 that forms the inductor 16 could be completely encapsulated in a relatively high dielectric constant material. This can include a number of thermal setting conductive polymers, glasses, silicones, ceramic or the like. Having a high dielectric constant material completely surrounding the wire 22 would tend to increase the turn-to-turn capacitance. In the art, this is known as parasitic capacitance. The total of all the parasitic capacitance $C_P$ shows up in parallel in the schematic diagram of FIG. 3. Accordingly, it is a feature of the present invention that the discrete capacitance C could be eliminated by having the parasitic capacitance $C_P$ sufficiently high enough to resonate with the inductance at the desired MRI RF pulsed frequency.

Figure 8:
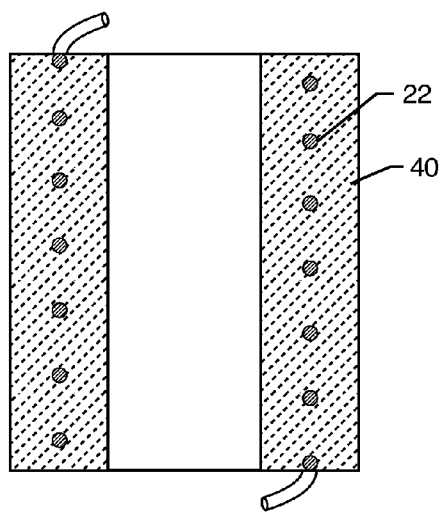
FIG. 8 is a sectional view taken generally along the line 8-8 of FIG. 7.
Figure 9:
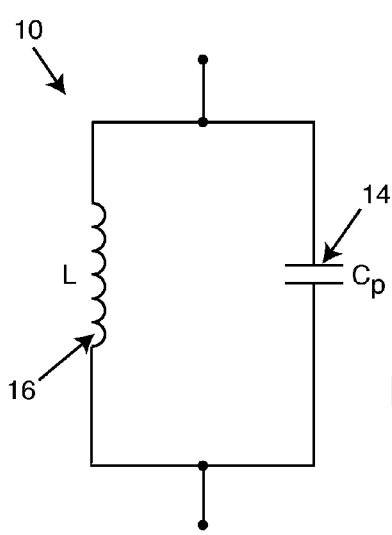
FIG. 9 is an electrical schematic of the bandstop filter of FIGS. 7 and 8.

This is better understood by referring to FIGS. 7-9 which illustrate an air wound solenoid type coil of wire 22 encapsulated within a body of dielectric material 40. The wire 22 can be of a biocompatible material, such as platinum, platinum iridium, MP-35N or the like. The encapsulated inductor assembly can be solid or hollow on the inside (tubular) as illustrated. The dielectric material 40 can be a thermal setting polymer, various coatings, a glass, a silicone, a ceramic or the like. By surrounding the coil or wire 22 with a high dielectric constant material 40 by molding, pressing, co-firing or the like, one greatly increases the parasitic capacitance $C_P$. This completely eliminates the need for a separate, discrete capacitive element. In other words, the coil or wire 22 along with the high dielectric material 40 forms its own resonant bandstop filter 10. The diagram shown in FIG. 9 shows how the parasitic capacitance $C_P$ ends up in parallel with the inductor element 16 thereby forming the novel L-C bandstop filter (tank) 10 of the present invention.

This invention allows for the creation of a bandstop filter for use in lead systems, using a single substrate body 12. This invention allows for small circuit design, more robust manufacturing, and higher strength through less joining operations.

Using cylindrical inductors provides the highest amount of volumetric efficiency. As described in the U.S. patent application Ser. No. 11/588,349, the inductance is key to balancing MRI protection with implantable medical device performance. Using cylindrical inductors is an effective way of maintaining high inductance and lower resistance.

Figure 10:
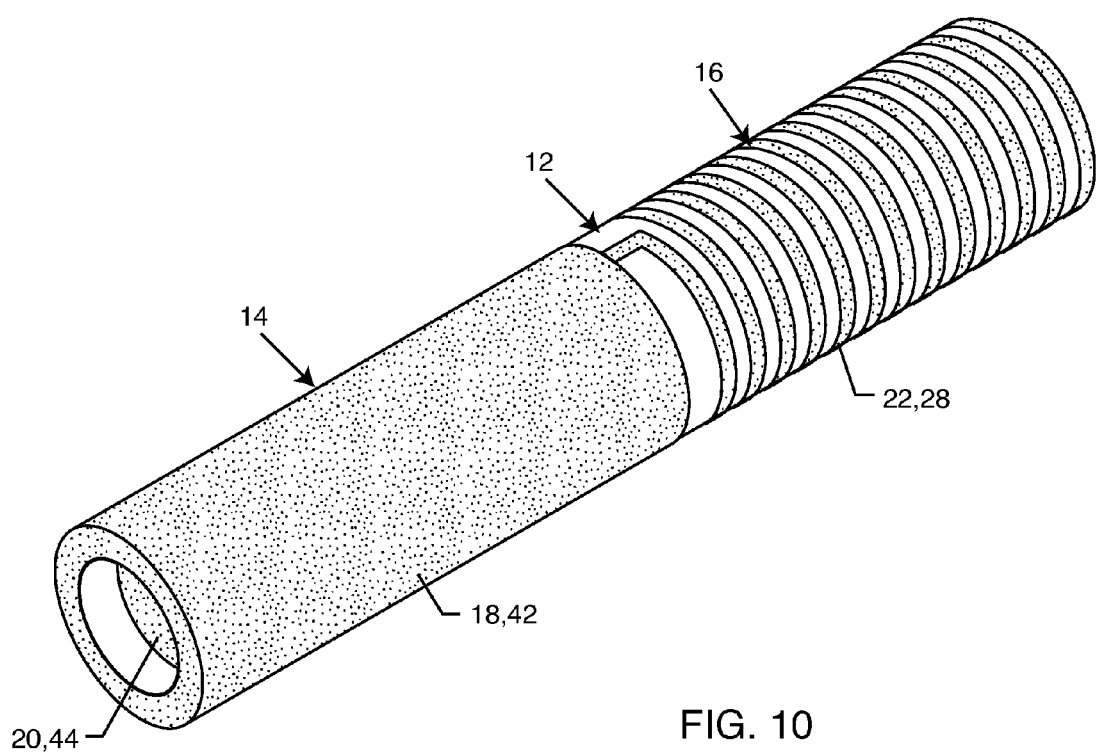
FIG. 10 is a perspective view of yet another alternative cylindrical bandstop filter for medical lead systems embodying the present invention.

FIG. 10 illustrates another type of cylindrical bandstop filter in accordance with the present invention. The dielectric body 12 (shown in FIGS. 11-13) is typically constructed of ceramic materials. One side, as illustrated the left hand side, is a typical single wall tubular capacitor 14. It has an outside diameter termination 42 which also forms the outside diameter capacitor electrode 18. There is also an inside diameter termination 44 which also forms the opposite capacitor electrode plate 20. The right hand side of this single walled tubular structure does not have the inside and outer capacitive termination. The right hand side has inductor windings 16, which can be discrete windings of very small wire 22 or inductor winding traces 28 that are deposited by photo lithography, photo etching, electroplating or the like.

The advantage of the structure shown in FIG. 10 is that the static field of the capacitor 14 is kept isolated from the magnetic field of the inductor 16. By connecting one end of the inductor 16 to the capacitor's outside diameter termination 42 and the other end to the capacitor's ID termination 44, this puts the capacitor 14 and inductor 16 in parallel, thereby forming the bandstop filter circuit 10 of the present invention. Referring once again to FIG. 10, another advantage of having the capacitor outside diameter metallization 42 and inside diameter metallization 44 away from the inductor is that one avoids the formation of eddy currents. Anytime that one places a metallic structure either inside or outside of an inductor solenoid, said metallic structure is immersed in the solenoid inductor's magnetic field. This tends to cause eddy currents and losses which are sometimes undesirable in the inductor component. Accordingly, the structure of FIG. 10 places the inductor and capacitor elements in parallel in accordance with the present invention, but mechanically places them in series thereby separating the capacitor's static field away from the magnetic field lines of the inductor element. The ID termination 44 can extend all the way to the right so that it can connect to the right hand inductor turn or it can be a thin trace or even a wire to further minimize eddy current effects. However, the outside diameter capacitor termination 42 only covers about half the length as shown.

Figure 11:
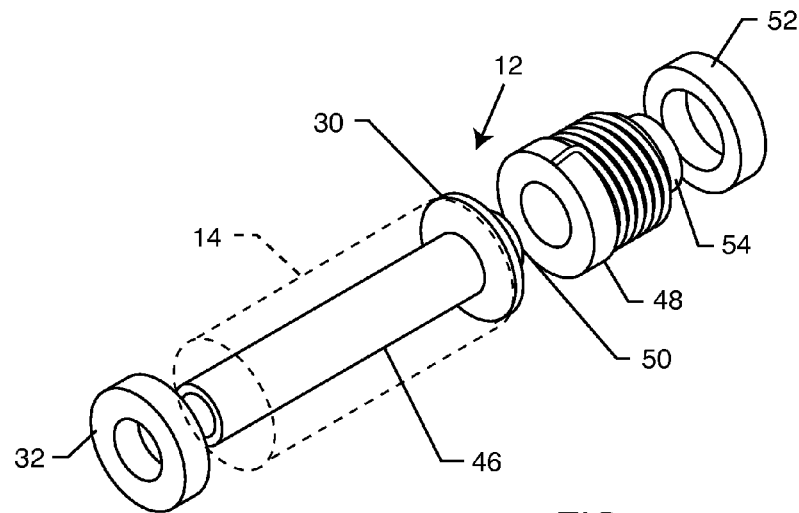
FIG. 11 is an exploded perspective view of various components forming the cylindrical bandstop filter shown in FIG. 10, wherein the tubular capacitor is shown in phantom.

FIG. 11 illustrates an exploded view of several components that would be very useful in manufacturing the substrate 12 used in the structure shown in FIG. 10. On the left hand side is the single wall tubular capacitor (shown in phantom) 14. As one can see, there is an end connector 32 on the left for convenient attachment to the capacitor's outside diameter termination 42. This end connector 32 is also convenient for attaching to a distal tip electrode or a lead wire.

There is also a conductive centerpiece or protrusion 46 which is electrically connected to the capacitor's inside diameter termination 44. The centerpiece protrusion 46 can be a one-piece or composite structure which includes an end connector 30. An insulative head structure 48 fits conveniently over a pedestal structure 50, helping to straightly align the entire assembly. The insulative head structure 48 is where the inductor wire 22 is wound. The insulative material can be of plastic, Delran, ceramic or any other insulative material. There is also a conductive connecting ring 52 which slips over a counter-bore 54. Again, this counter-bore 54 keeps the various components of this assembly in good alignment, which is important due to the very small size of this overall parallel resonant bandstop filter.

Connecting rings 32 and 52 are typically of the group of biocompatible materials, including platinum, platinum iridium, titanium or the like. The end caps 32 and 52 are convenient for laser welding of typical implantable lead wires such as MP-35N. The interface between features 30, 32 and 52 could also incorporate interlocking castle heads to increase the torsional strength. This is particularly important when the overall bandstop filter assembly would be used in a pacemaker active fixation tip assembly.

Figure 12:
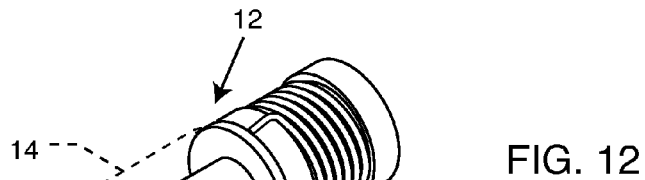
FIG. 12 is a perspective view similar to FIG. 11, wherein the various components of the tubular substrate have been assembled and are ready to accept the tubular capacitor and the inductor winding turns.
Figure 13:
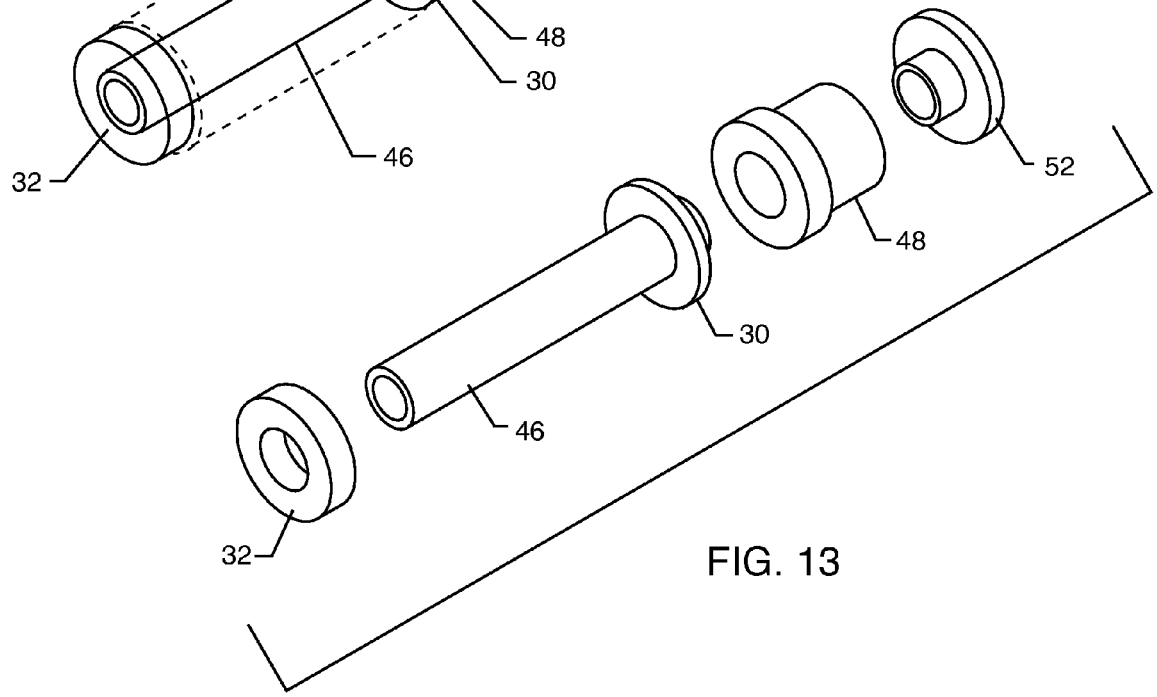
FIG. 13 is an exploded perspective view similar to FIG. 11, illustrating an alternative configuration of parts forming the tubular substrate.

FIG. 12 illustrates the same structure as FIG. 11 except in this case, all of the various component features have been assembled. FIG. 13 is very similar to FIGS. 11 and 12, but illustrates that there are various ways to create counter-bores and pedestals to maintain the alignment and fit of the component pieces of the assembly 12.

FIG. 14 illustrates yet another embodiment where the inductor 16 can be wound around a metal or plastic substrate 12 having a protrusion 56 which is inserted into the inside diameter of a single wall tubular capacitor 14. The protruding section 56 of the substrate 12, if made of plastic, would typically be metal plated or sputtered so as to be conductive. This allows for an electrical connection by means of a conductive adhesive 58 or the like to the capacitor inside diameter termination/electrode 18. The end connector 32 is designed to attach electrically to the capacitor's outside diameter termination/electrode 20.

FIG. 15 is a cross-sectional view of the assembled components taken along the line 15-15 of FIG. 14. One can see that there are four important electrical connections as illustrated. $E_1$ is the electrical connection between the end connector 30 and the inductor wire 22. Electrical connection $E_2$ connects the opposite end of the inductor lead wire 22 to the capacitor's outside diameter metallization/electrode 20. Electrical connection $E_3$ connects the capacitor's inside diameter metallization/electrode 18 to the metallic structure 30 on which the inductor 16 is wound. Electrical connection $E_4$ connects end connector 32 to the capacitor's outside diameter metallization 20. This places the inductor portion and the tubular capacitor portion of the assembly in parallel with one another. End connectors 30 and 32, as previously mentioned, are biocompatible and are suitable for laser weld attachment of typical human implantable lead wires, such as might comprise alloy MP-35N.

Aside from the methods described previously, biocompatibility can be achieved in one of several ways. The first is to use biocompatible components, such as alumina, porcelain, gold, platinum, and the like, such that no actual biocompatible "hermetic seal" is required. The second option is to coat the entire system with a known biocompatible material, such as PMMA, SIC, silicone, paralyne, polyimide or the like. Using biocompatible protective coatings over non-biocompatible materials will greatly reduce the cost of the cylindrical bandstop filter. For example, instead of using platinum lead wires for the inductor element, one could use a much less expensive material such as copper. This would serve two benefits, in that it would provide biocompatibility, and it would provide an insulative layer to prevent accidental shorting of the system. The third option is to include a tube (later described in FIGS. 16-20), either metal or ceramic, which can be brazed, soldered, or welded between the two cylindrical connectors. As it would completely cover the cylindrical bandstop filters described, it would provide a biocompatible and electrical barrier between the filter's outer surface and body fluid.

Figure 16:
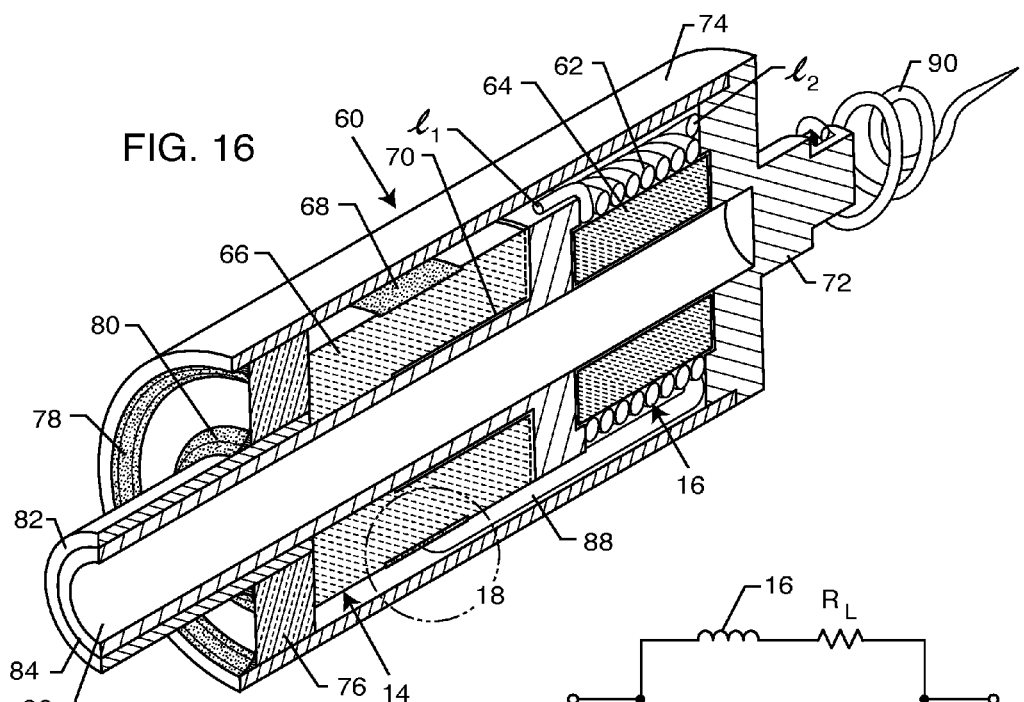
FIG. 16 is sectioned perspective view of a medical lead bandstop filter embodying the present invention and hermetically sealed within a container having a tube extending therefrom, in accordance with the present invention.

FIG. 16 is a hermetically sealed cylindrical bandstop filter 60 embodying the present invention. In this case, the inductor winding 62 is wound around a plastic or non-ferromagnetic core 64. The capacitor 16 is formed by a prior art tubular capacitor consisting of dielectric 66, an external electrode metallization 68 and an internal inside diameter metallization surface 70. As before, the overlap of these metallized areas 68 and 70 form the effective capacitance area.

The sensitive capacitor 14 and inductive 16 components in FIG. 16 have been hermetically sealed using biocompatible components such that complete protection against body fluids is provided. The hermetic seal on the right hand side is formed between end plate 72 and the outside diameter of conductive cylinder 74. Preferred materials for the cylindrical end cap 72 and the outside diameter cylinder 74 are titanium. However, it will be obvious to those skilled in the art that many other materials could be used. In certain embodiments, even a ceramic material could be used for cylinder 74 as long as a jumper wire is used as will be described further.

Referring once again to FIG. 16, one can see that on the left hand end, there is a traditional hermetic seal consisting of an alumina or any ceramic insulator 76 which is gold brazed to the outside diameter metallized cylinder 74. There is also an inside diameter gold braze 80 which is formed between an outer tubelet 82 and the ceramic insulator surface 76. As is well known in the prior art, the ceramic insulator is sputtered such that it can receive gold brazing. Alternative materials, of course, for hermetic seals include glass and various glass composites. It will be obvious to those skilled in the art that an end plate 72 similar to on the right side could also be substituted on the left and visa versa. A laser weld 84 is typically preformed between the inner and outer tubelets 82 and 86 thereby completing the hermetic seal. The inner tubelet 86 passes through the center of the capacitor 14 and is in electrical conductive relationship with the capacitor's inside diameter metallization 70.

Referring now to the inductor 16, one can see that one end of the inductor windings 62 is electrically attached via $e_1$ to metal tubelet 86 that passes through the capacitor's inside diameter. Accordingly, the inductor 16 is effectively electrically connected to the capacitor inside diameter metallization 70. The other end of the inductor is connected via electrical connection $e_2$ to end plate 72. There is also an electrical jumper wire 88 which also connects the end plate 72 to the tubular capacitor's outside diameter metallization 68.

Figure 17:
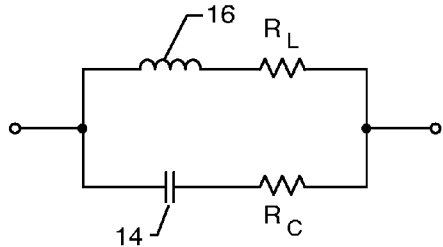
FIG. 17 is an electric schematic of the bandstop filter of FIG. 16.

FIG. 17 is the resulting schematic diagram of the structure that was previously described in FIG. 16. $R_L$ and $R_C$ are the resistive losses of the inductor and the capacitor respectively.

Figure 18:
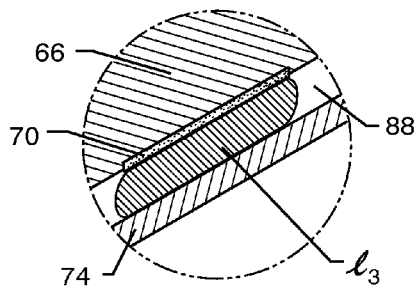
FIG. 18 is an enlarged cross-sectional view of area "18", illustrating connection of an inductor winding to an electrode of the capacitor, in accordance with the present invention.

FIG. 18 is an exploded alternative view which illuminates the elimination of jumper wire 88. In this case, an electrical connection $e_3$ is formed between the capacitor's outside diameter metallization 70 and the conductive cylinder 74. In this case, the conductive cylinder itself forms the same electrical function as the jumper wire in that it connects the capacitor's outside diameter metallization 70 to end plate 72.

Referring once again to FIG. 16, one can see that the tubelet 86 can be either solid or hollow. As shown, it is hollow to adapt to one type of insertion wire that is first guided through the venous system. Tubelet 86 could also be a hex or other type head for convenient screw-in by some sort of a surgical tool.

The distal electrode 90 is shown as a helix tip which is typically screwed into body tissue and firmly affixed. The tip 90 could also be the continuation of, for example, a pacemaker lead wire. Accordingly, the structure shown in FIG. 16 could be placed at the distal tip or anywhere along the length of an implanted lead wire system.

Figure 19:
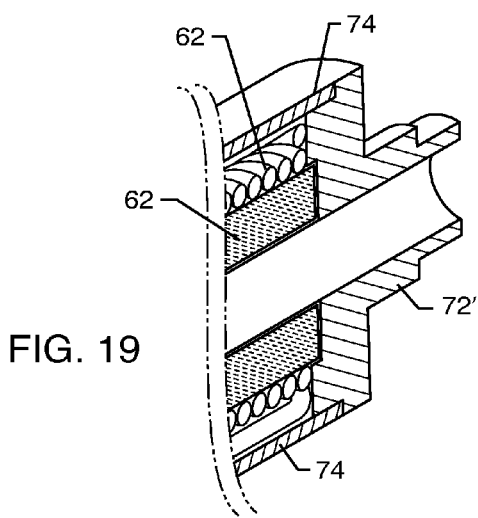
FIG. 19 is a fragmented cross-sectional view of an alternative end for the structure of FIG. 16.

FIG. 19 is an alternative view taken from the right end of FIG. 16 showing that the tubelet 86 and end cap 72' could be hollow all the way through. This is particularly convenient for certain types of guide wires which are first inserted into the venous system and then the final active implantable medical device lead wire system is literally threaded along the guide wire which is later removed.

Figure 20:
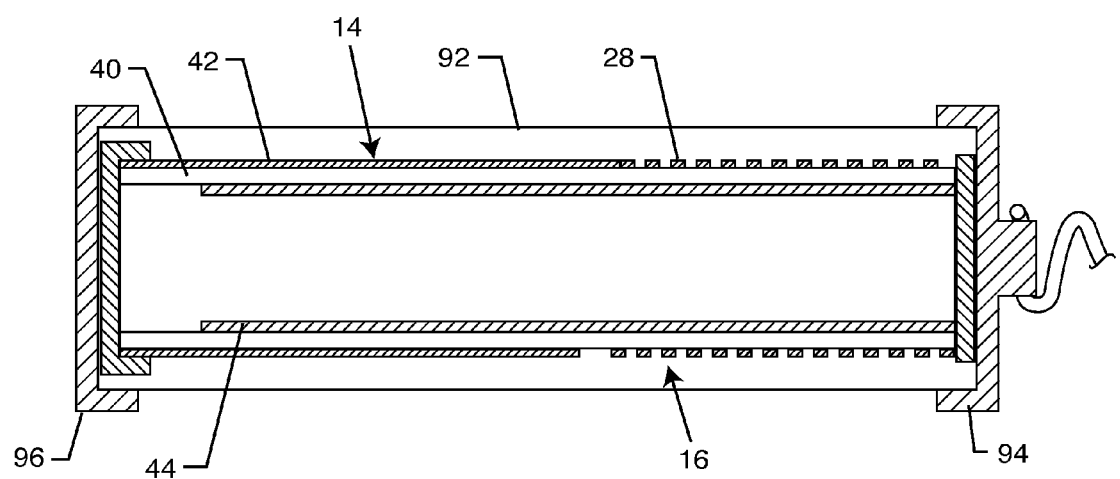
FIG. 20 is a cross-sectional view of the medical lead bandstop filter of FIG. 10, disposed within a hermetically sealed container, in accordance with the present invention.

FIG. 20 illustrates the novel parallel capacitor and inductor combination that was previously described in FIG. 10, but is now integrated into a hermetic package. The outside diameter cylinder 92 can be of various materials, including a hermetic ceramic structure, glass structure or the like. The inductor 16 is connected on the top end to end plate 94 and to the capacitor's inside diameter metallization 44. The capacitor's outside diameter metallization 42 is in turn electrically connected to the opposite end cap 96. This has the effect of putting the capacitor 14 in parallel with the inductor 16 in accordance with the present invention. It will be obvious to those skilled in the art that structure 96 is shown as an end plate, however, in accordance with the present invention, a variety of structures similar to end plate 94 or a hermetic seal 76, as described in FIG. 16, could be used instead.

It will be appreciated by those skilled in the art that the hermetically sealed cylindrical structures of FIGS. 16 and 20 can be used to hermetically seal not only the bandstop filter of FIG. 10, but also FIGS. 1, 2, 4, 5 and 7. The capacitor 14 and inductor 16 structures could be placed within cylinder 74 with end caps 72 and 76 used to hermetically seal the filter. Alternatively, the structures could be placed within cylinder 92 having end caps 94 and 96. In any event, the capacitor 14 and inductor 16 would be placed in series with the medical lead wire or electrode by conductively coupling a first end of the inductor winding to the first end cap, and a second end of the inductor winding to the second end cap. In the instance of the embodiment illustrated in FIGS. 1 and 2, the tubes 82 and 86 could extend into the hermetic structure so as to provide conductive coupling to the inner electrode of the tubular capacitor. In any event, the electrodes of the tubular capacitor would be conductively coupled to the end caps so as to place the bandstop filter in series with the medical lead wire and/or electrode.

Although several embodiments have been described in some detail for purposes of illustration, various modifications may be made without departing from the scope and spirit of the invention. Accordingly, the invention is not to be limited, except as by the appended claims.

What is claimed is:

1. A medical lead bandstop filter for attenuating current flow through a lead wire at a selected frequency, comprising:
   a tubular capacitor having a first electrode and a second electrode; and
   a generally cylindrical inductor attached in series at an end of the capacitor, the inductor including a winding having a first end conductively coupled to the first electrode and a second end conductively coupled to the second electrode so as to place the capacitor and the inductor electrically in parallel with one another, wherein values of capacitance and inductance are selected such that the bandstop filter is resonant at the selected frequency.

2. The medical lead bandstop filter of claim 1, wherein the selected frequency comprises a range of selected frequencies.

3. The medical lead bandstop filter of claim 2, wherein the selected range of frequencies correspond to a plurality of MRI pulsed frequencies.

4. The medical lead bandstop filter of claim 1, wherein the inductor includes a protruding section extending into an adjacent end of the capacitor.

5. The medical lead bandstop filter of claim 4, wherein the protruding section comprises a conductive material conductively coupled to the first electrode.

6. The medical lead bandstop filter of claim 4, wherein the inductor includes a head section comprised of insulative material coupled to the protruding section and associated with the winding.

7. The medical lead bandstop filter of claim 6, wherein the winding comprises a conductive circuit trace or wire attached to an outer surface of the head section.

8. The medical lead bandstop filter of claim 1, including a first end cap conductively coupled to the first end of the winding and the first electrode, and a second end cap conductively coupled to the second end of the winding and the second electrode.

9. The medical lead bandstop filter of claim 1, wherein electrical components thereof are hermetically insulated from contact with biological fluids or cells.

10. The medical lead bandstop filter of claim 9, wherein the bandstop filter is disposed within a biocompatible cylinder having a first biocompatible end cap attached to a first end thereof, and a second biocompatible end cap attached to a second end thereof so as to prevent body fluids or cells from entering therein.

11. The medical lead bandstop filter of claim 10, wherein the first end of inductor winding and the capacitor first electrode are conductively coupled to the first end cap, and the second end of the inductor and the capacitor second electrode are conductively coupled to the second end cap.

12. The medical lead bandstop filter of claim 11, wherein the first and second end caps are adapted to be conductively coupled to the lead wire or an electrode of a medical lead system.

13. The medical lead bandstop filter of claim 11, including a tube extending through the first end cap and into the cylinder so as to be conductively coupled to the first electrode.

14. The medical lead bandstop filter of claim 13, wherein the tube extends through the cylinder and the second end cap.

15. The medical lead bandstop filter of claim 9, wherein the bandstop filter is hermetically sealed within a biocompatible material coating the bandstop filter.

16. The medical lead bandstop filter of claim 1, wherein the bandstop filter is comprised of biocompatible materials.

17. A medical lead bandstop filter for attenuating current flow through a lead wire at a selected frequency, comprising:
   a generally cylindrical dielectric body; and
   a conductive winding associated with the body, the conductive winding and the body cooperatively forming an inductor;
      wherein turns of the conductive winding form a parasitic capacitor in parallel with the inductor, and wherein values of capacitance and inductance are selected such that the bandstop filter is resonant at the selected frequency.

18. The medical lead bandstop filter of claim 17, wherein the selected frequency comprises a range of selected frequencies.

19. The medical lead bandstop filter of claim 18, wherein the selected range of frequencies correspond to a plurality of MRI pulsed frequencies.

20. The medical lead bandstop filter of claim 17, wherein the generally cylindrical dielectric body is tubular.

21. The medical lead bandstop filter of claim 17, wherein the conductive winding is attached to an outer surface of the body.

22. The medical lead bandstop filter of claim 17, wherein the conductive winding comprises conductive wire, a conductive circuit trace, or is embedded within the dielectric body.

23. The medical lead bandstop filter of claim 17, wherein electrical components thereof are hermetically insulated from contact with biological fluids or cells.

24. The medical lead bandstop filter of claim 23, wherein the bandstop filter is disposed within a biocompatible cylinder having a first biocompatible end cap attached to a first end thereof, and a second biocompatible end cap attached to a second end thereof so as to prevent body fluids or cells from entering therein.

25. The medical lead bandstop filter of claim 24, wherein the first end of inductor winding is conductively coupled to the first end cap, and the second end of the inductor winding is conductively coupled to the second end cap.

26. The medical lead bandstop filter of claim 24, wherein the first and second end caps are adapted to be conductively coupled to the lead wire or an electrode of a medical lead system.

27. The medical lead bandstop filter of claim 23, wherein the bandstop filter is hermetically sealed within a biocompatible material coating the bandstop filter.

28. The medical lead bandstop filter of claim 17, wherein the bandstop filter is comprised of biocompatible materials.

29. A medical lead bandstop filter for attenuating current flow through a lead wire at a selected frequency, comprising:
   a tubular capacitor having a first electrode and a second electrode; and
   a conductive winding wound around the capacitor and forming an inductor, a first end of the winding being conductively coupled to the first electrode and a second end of the winding being conductively coupled to the second electrode so as to place the capacitor and the inductor in parallel with one another, wherein values of capacitance and inductance are selected such that the bandstop filter is resonant at the selected frequency.

30. The medical lead bandstop filter of claim 29, wherein the selected frequency comprises a range of selected frequencies.

31. The medical lead bandstop filter of claim 30, wherein the selected range of frequencies correspond to a plurality of MRI pulsed frequencies.

32. The medical lead bandstop filter of claim 29, wherein the first electrode comprises a first set of electrode plates and the second electrode comprises a second set of electrode plates in spaced apart and overlapping relation with the first set of electrode plates.

33. The medical lead bandstop filter of claim 29, wherein the conductive winding comprises a wire attached to an outer surface of the tubular capacitor.

34. The medical lead bandstop filter of claim 29, wherein the conductive winding comprises a conductive circuit trace attached to an outer surface of the tubular capacitor.

35. The medical lead bandstop filter of claim 29, wherein electrical components thereof are hermetically insulated from contact with biological fluids or cells.

36. The medical lead bandstop filter of claim 35, wherein the bandstop filter is disposed within a biocompatible cylinder having a first biocompatible end cap attached to a first end thereof, and a second biocompatible end cap attached to a second end thereof so as to prevent body fluids or cells from entering therein.

37. The medical lead bandstop filter of claim 36, wherein the first end of inductor winding and the capacitor first electrode are conductively coupled to the first end cap, and the second end of the inductor and the capacitor second electrode are conductively coupled to the second end cap.

38. The medical lead bandstop filter of claim 36, wherein the first and second end caps are adapted to be conductively coupled to the lead wire or an electrode of a medical lead system.

39. The medical lead bandstop filter of claim 36, including a tube extending through the first end cap and into the cylinder so as to be conductively coupled to the first electrode.

40. The medical lead bandstop filter of claim 39, wherein the tube extends through the cylinder and the second end cap.

41. The medical lead bandstop filter of claim 35, wherein the bandstop filter is hermetically sealed within a biocompatible material coating the bandstop filter.

42. The medical lead bandstop filter of claim 29, wherein the bandstop filter is comprised of biocompatible materials.

\* \* \* \* \*